United States Patent
Foo et al.

(10) Patent No.: US 9,554,707 B2
(45) Date of Patent: Jan. 31, 2017

(54) CONCURRENT ACQUISITION OF PET FIELDS DURING ACQUISITION OF A MRI FIELD OF VIEW

(75) Inventors: Thomas Kwok-Fah Foo, Clifton Park, NY (US); Christopher Judson Hardy, Niskayuna, NY (US); Manjeshwar Mohan Ravindra, Glenville, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/539,240

(22) Filed: Jun. 29, 2012

(65) Prior Publication Data

US 2014/0005520 A1    Jan. 2, 2014

(51) Int. Cl.
| | |
|---|---|
| A61B 5/00 | (2006.01) |
| A61B 5/055 | (2006.01) |
| G01R 33/483 | (2006.01) |
| G01R 33/48 | (2006.01) |
| A61B 6/03 | (2006.01) |
| A61B 6/00 | (2006.01) |

(Continued)

(52) U.S. Cl.
CPC ............. *A61B 5/0035* (2013.01); *A61B 5/055* (2013.01); *A61B 6/037* (2013.01); *A61B 6/4417* (2013.01); *G01R 33/481* (2013.01); *G01R 33/483* (2013.01); *G01R 33/4824* (2013.01); *G01R 33/546* (2013.01); *G01R 33/56383* (2013.01)

(58) Field of Classification Search
CPC ............ G06T 2207/10088; G06T 2207/10104; A61N 2005/1052; A61N 2005/1055; G01R 33/481
See application file for complete search history.

(56) References Cited

U.S. PATENT DOCUMENTS

| | | | | |
|---|---|---|---|---|
| 6,794,869 | B2* | 9/2004 | Brittain | 324/309 |
| 6,975,113 | B1* | 12/2005 | Gurr | 324/309 |

(Continued)

FOREIGN PATENT DOCUMENTS

| | | |
|---|---|---|
| CN | 101132731 A | 2/2008 |
| CN | 101254134 A | 9/2008 |
| CN | 101310687 A | 11/2008 |

OTHER PUBLICATIONS

Kruger DG, et al. Continuously moving table data acquisition method for long FOV contrast enhanced MRA and whole body MRI. Magn Reson Med 2001;47:224-231.

(Continued)

*Primary Examiner* — Bo J Peng
(74) *Attorney, Agent, or Firm* — Joseph F. Harding; The Small Patent Law Group LLC

(57) ABSTRACT

Exemplary embodiments are directed to acquiring multiple sets of positron emission tomography (PET) data for different areas of a subject concurrently with acquiring portions of a single magnetic resonance field of view. Positron emission tomography (PET) images and magnetic resonance (MR) images can be acquired using a combined PET-MRI scanner, wherein, for example, a first portion of MR data from a MR field of view can be acquired concurrently with a first acquisition of PET data, a position of the MR field of view can be adjusted in response to a change in a location of a bed in the combined PET-MRI scanner, and a second portion of MR data from the MR field of view can be acquired concurrently with a second acquisition of PET data.

18 Claims, 5 Drawing Sheets

(51) Int. Cl.
*G01R 33/54* (2006.01)
*G01R 33/563* (2006.01)

(56) References Cited

U.S. PATENT DOCUMENTS

| | | | |
|---|---|---|---|
| 7,667,457 | B2 | 2/2010 | Linz et al. |
| 7,847,552 | B2 | 12/2010 | Haworth et al. |
| 2007/0055127 | A1* | 3/2007 | Ladebeck ............ G01R 33/481 600/407 |
| 2007/0102641 | A1 | 5/2007 | Schmand et al. |
| 2008/0048659 | A1* | 2/2008 | Reeder .......................... 324/312 |
| 2008/0088309 | A1* | 4/2008 | Eberler ................ G01R 33/481 324/318 |
| 2008/0214929 | A1 | 9/2008 | Martin et al. |
| 2008/0298664 | A1 | 12/2008 | Martin et al. |
| 2009/0182219 | A1* | 7/2009 | Gericke et al. ............... 600/407 |
| 2010/0013479 | A1* | 1/2010 | Park .............................. 324/309 |
| 2010/0033186 | A1 | 2/2010 | Overweg et al. |
| 2010/0152577 | A1 | 6/2010 | Young et al. |
| 2010/0217112 | A1 | 8/2010 | Choi et al. |
| 2010/0219347 | A1 | 9/2010 | Schulz et al. |
| 2011/0080168 | A1 | 4/2011 | Fenchel et al. |
| 2011/0103669 | A1 | 5/2011 | Michel et al. |
| 2011/0224534 | A1 | 9/2011 | Yamaya et al. |
| 2012/0022362 | A1 | 1/2012 | Caruba et al. |

OTHER PUBLICATIONS

Noll DC, et al. Homodyne Detection in Magnetic Resonance Imaging, IEEE Transactions on Medical Imaging 1991;10:154-163.
Unofficial English translation of Office Action and Search Report issued in connection with corresponding CN Application No. 201310266016.2 on Jul. 4, 2016.

* cited by examiner

CONCURRENT ACQUISITION OF PET FIELDS DURING ACQUISITION OF A MRI FIELD OF VIEW

BACKGROUND

Positron Emission Tomography (PET) imaging involves the creation of tomographic images of positron emitting radionuclides in a subject of interest. Conventionally, subject (e.g., a human patient) receives a PET agent, e.g., a radiopharmaceutical, and the subject is positioned within a PET imaging system that includes a detector and detection electronics. As the PET agent decays, positively charged anti-electrons (positrons) are emitted. For commonly used PET agents the positrons travel a few millimeters through the tissues of the subject before colliding with an electron, resulting in mutual annihilation. The positron/electron annihilation results in a pair of oppositely-directed gamma rays with approximately 511 keV energy.

When the gamma rays impinge on the detector, the detector emits light, which is detected by detection electronics. The signals corresponding to the emitted light are processed as incidences of gamma rays. When two gamma rays strike oppositely positioned scintillators of the detector at approximately the same time, a coincidence is registered. The coincidences are processed to identify true coincidence events, which are binned and integrated to form frames of PET data that can be reconstructed as images depicting the distribution of the PET agent in the subject.

Another technique employed in medical imaging is Magnetic Resonance Imaging (MRI), which conventionally uses a powerful magnet to create a strong, uniform, static magnetic field (i.e., the "main magnetic field") to polarize hydrogen nuclei in a subject's tissue so that the magnetic moments generally align along the direction of the main magnetic field. MRI systems conventionally include gradient coils that produce smaller amplitude (i.e. compared to the main magnetic field), spatially varying magnetic fields in response to an electric current control signal. Typically, gradient coils are designed to produce a magnetic field component that is generally aligned along the axis of the main magnetic field and that varies in amplitude with position along one or more axes. The effect of a gradient coil is to create a small ramp on the magnetic field strength and concomitantly on the resonant frequency of the nuclear spins, along a single axis. Three gradient coils with orthogonal axes are typically used to "spatially encode" the MR signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal, which can be detected by the MRI system as MR data, and combined with multiple additional such signals may be used to reconstruct an MR image using a computer and known algorithms.

In recent years, hybrid or combined PET-MRI scanners have been developed so that PET and MRI images can be acquired using a single medical imaging scanner. While these conventional combined PET-MRI scanners can offer efficiencies over separate and individual PET scanners and MRI scanners, the combination of the PET and MRI scanners into a single scanner present difficult challenges in realizing such efficiencies and ensuring high quality image acquisition.

SUMMARY

Exemplary embodiments of the present disclosure are directed to acquiring multiple sets of positron emission tomography (PET) data for different areas of a subject concurrently with acquiring portions of data from a single magnetic resonance field of view. MR data acquisition can be partitioned across a sequence of PET data acquisitions to realize efficiencies of a combined PET-MRI scanner because MR data acquisitions can require a greater amount of time than PET data acquisitions. In exemplary embodiments, because only a portion of the MR data is acquired for a specified field of view when a PET data acquisition is performed, the overall time required to perform a scan sequence can be reduced over conventional approaches.

In one embodiment a combined positron emission tomography (PET) and magnetic resonance imaging (MRI) system is disclosed. The system includes PET imaging components, MRI components, and a controller. The PET imaging components form a PET scanner portion and the MRI components form an MRI scanner portion of the combined PET-MRI scanner. The controller is in communication with the PET imaging components and the MRI components to control the MRI scanner portion to partition an acquisition of MR data for a specified field of view over a sequence of PET data acquisitions to acquire the MR data for the field of view concurrently with an acquisition of different sets of PET data.

In some embodiments, the system can include a support structure (e.g., a bed or table for supporting a subject to be imaged) disposed and moveable with respect to a PET spatial coverage region associated with the PET scanner portion and a MRI spatial coverage region associated with the MRI scanner portion. The controller can be programmed to control acquisition of PET data and MR data based on a position of the support structure. An acquisition of the MR data for the field of view can be apportioned over at least two positions of the support structure. A first PET data acquisition in the sequence of PET acquisitions can be performed at a first one of the at least two positions. A second PET data acquisition in the sequence of PET acquisitions can be performed at a second one of the at least two positions. The MR data acquired with respect to the first position can represent a first portion (e.g. half) of a k-space and the MR data acquired with respect to the second position can represent a second portion (e.g., a remaining half) of the k-space. In some embodiments, the controller is programmed to control the MRI scanner portion to acquire the first portion of the k-space concurrently with the first PET data acquisition and to acquire the second portion of k-space concurrently with the second PET data acquisition.

In another embodiment, a method of capturing positron emission tomography (PET) images and magnetic resonance (MR) images with a combined PET-MRI scanner is disclosed. The method includes acquiring a first portion of MR data from an MR field of view concurrently with a first acquisition of PET data, adjusting a position of the MR field of view to compensate for a change in a location of a bed of the combined PET-MRI scanner and thus maintain the MR field of view over the same portion of the anatomy, while acquiring a second portion of MR data from the MR field of view concurrently with a second acquisition of PET data. In some embodiments, a position of the MR field of view can be adjusted in response to another change in the location of the bed of the combined PET-MRI scanner while a third portion of MR data can be acquired from the MR field of view concurrently with a third acquisition of PET data.

In some embodiments, the first portion of MR data acquired from the field of view represents a first portion of k-space and the second portion of MR data acquired from the field of view represents a second portion of k-space. The first portion of k-space can correspond to half of k-space and the second portion of k-space can correspond to a remaining half of k-space.

In some embodiments, the method can also include reconstructing the first portion of MR data acquired from the field of view to generate a first stack of complex MR images, reconstructing the second portion of MR data acquired from the field of view to generate a second stack of complex MR images, and combining the first and second stacks to form a single stack of MR images having reduced aliasing in comparison to the first and second stacks. The MR images of the first and second stacks can be unwarped prior to combining the first and second stacks.

In some embodiments, the method can also include first combining the first and second portions of MR data from the field of view and then reconstructing the full set of MR data acquired from the field of view to generate a stack of MR images.

In some embodiments, adjusting a position of the MR field of view for the second portion of the MR data acquisition from the field of view can be performed by shifting the field of view to align the field of view with an area of a subject for which the first portion of the MR data from the field of view was acquired. The field of view can be shifted by at least one of adjusting an MR receiver frequency of the combined PET-MRI scanner or adjusting a phase of MR signal reception of the MR receiver.

In some embodiments, the MR data can be acquired as a Cartesian k-space or as a non-Cartesian k-space.

Any combination or permutation of embodiments is envisaged. Other objects and features will become apparent from the following detailed description considered in conjunction with the accompanying drawings. It is to be understood, however, that the drawings are designed as an illustration only and not as a definition of the limits of the invention.

DESCRIPTION OF EXEMPLARY EMBODIMENTS

Exemplary embodiments of the present disclosure are directed to acquiring multiple sets of positron emission tomography (PET) data for different areas of a subject concurrently with acquiring portions of data from a single magnetic resonance field of view. For example, exemplary embodiments of the present disclosure can acquire a first portion of MR data from an MR field of view concurrently with a first acquisition of PET data and can acquire a second portion of MR data from the MR field of view concurrently with a second acquisition of PET data. A position of the bed can be changed between the acquisitions such that PET data of different areas of a subject can be acquired while MR data corresponding to an identical or substantially identical area of the subject can be acquired over the different bed positions.

By partitioning the MR data acquisition across a sequence of PET data acquisitions, efficiencies of a combined PET-MRI scanner can be realized since MR data acquisition can be require a greater amount of time than PET data acquisitions. In exemplary embodiments, because only a portion of the MR data is acquired for a specified field of view when a PET data acquisition is performed, the overall time required to perform a scan sequence can be reduced over conventional approaches.

As used herein, "concurrently" refers to acquiring PET data and MR data within the same period of time. The data can be acquired simultaneously (i.e. at the same time), can be acquired substantially simultaneously (i.e., at approximately the same time), can be acquired in an interleaved manner where acquisition switches back and forth between PET data acquisition and MR data acquisition, and/or can be otherwise acquired within the same time period.

Figure 1:
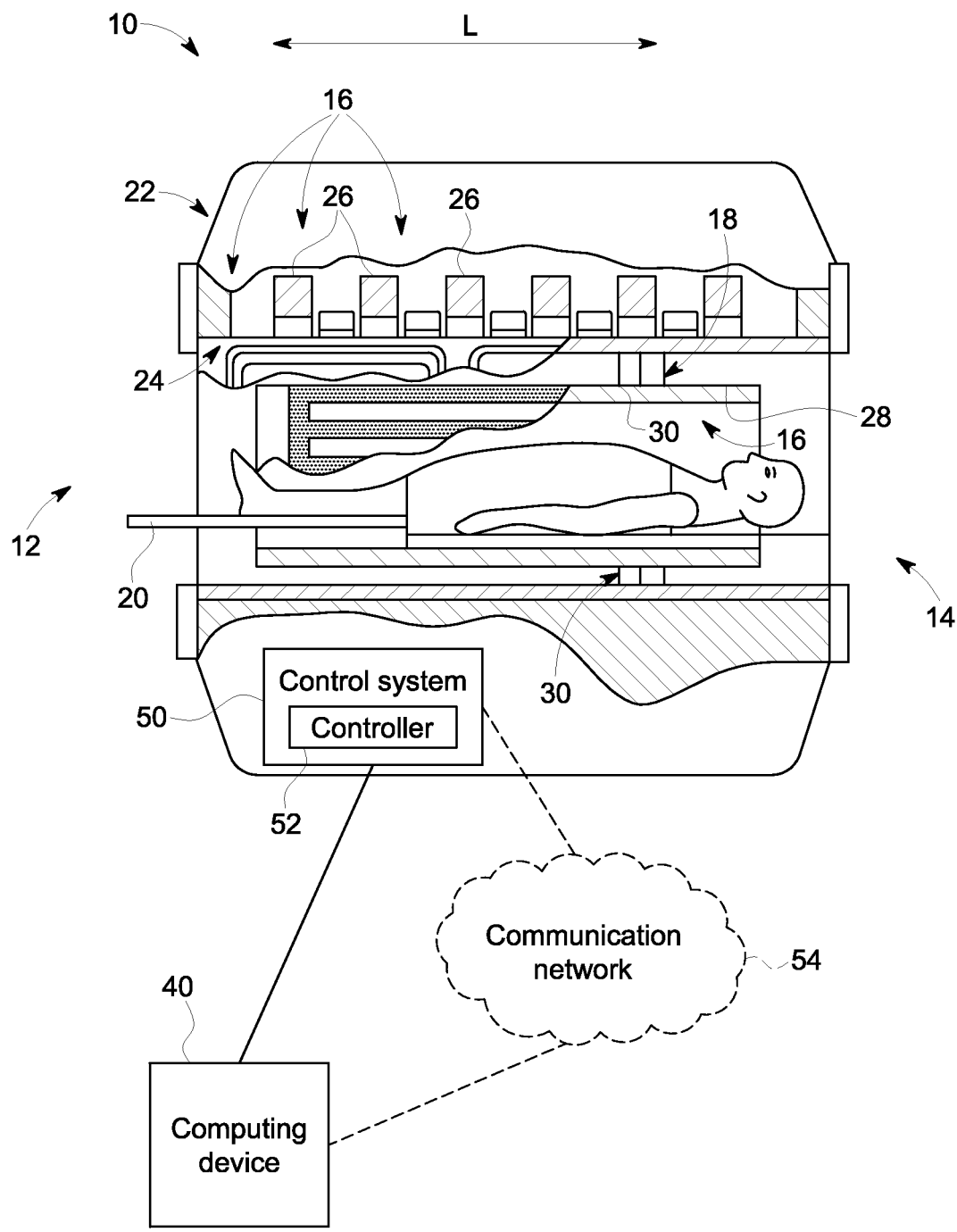
FIG. 1 illustrates an exemplary combined PET-MRI scanner in accordance with exemplary embodiments of the present disclosure.

FIG. 1 is illustrative of a hybrid or combined Positron Emission Tomography (PET)-Magnetic Resonance Imaging (MRI) scanner 10. The scanner 10 can generally extend longitudinally along a longitudinal axis L from a proximal end 12 to the distal end 14. The scanner 10 can include MRI components 16 forming an MRI scanner portion configured to acquire MR data, PET imaging components 18 forming a PET image scanner portion configured to acquire PET image data, and a support structure, e.g., a bed 20 (or table), configured to translate along the longitudinal axis L from the proximal end 12 to the distal end 14 to position the bed 20 with respect to the MRI components 16 and the PET imaging components 18. In some embodiments, a spatial coverage region associated with MRI components 16, e.g., a maximum longitudinal distance over which a single MR data acquisition can be performed, and a spatial coverage associated with the PET components 18, e.g., a maximum longitudinal distance over which a single PET acquisition can be performed, can be different. For example, in one exemplary embodiment, a single MR data acquisition can cover, e.g., approximately 60 cm, while a single PET acquisition can cover, e.g., approximately 25 cm in the longitudinal direction.

The MRI components 16 can include a magnet assembly 22 and a gradient coil assembly 24, which can be implemented separately or as part of the magnet assembly 22. The magnet assembly 22 can include a polarizing main magnet 26 and a coil assembly 28, which can be implemented as a radio frequency (RF) coil and a phased array receive coil.

The coil assembly 28 of the magnet assembly 22 can be configured to transmit stimulus pulses and to receive excitation pulses radiating from the subject in response to the stimulus pulses. The gradient assembly 24 can include one or more physical gradient coils (e.g., three gradient coils having orthogonal axes) to produce magnetic field gradients to spatially encode acquired MR data output from the scanner 10 according to a k-space or raw data matrix. In exemplary embodiments, one or more k-trajectories can be implemented, such as a Cartesian k-trajectory, spiral k-trajectory, cone k-trajectory, radial k-trajectory, and/or any other suitable k-trajectory.

The PET imaging components 18 of the scanner 10 can include a positron emission detector 30, configured to detect gamma rays from positron annihilations emitted from a subject. Detector 30 can include scintillators and photovoltaic detection electronics. The detector 30 can be of any suitable construction and have any suitable arrangement for acquiring PET data. For example, in exemplary embodiments, the detector 30 can have a ring configuration. Gamma ray incidences detected by the scintillators of the detector 30 can be transformed, by the photovoltaic detection electronics of the detector 30, into electrical signals, which can be conditioned and processed to output digital signals that can match gamma ray detections as potential coincidence events. When two gamma rays strike detectors approximately opposite one another, it is possible, absent the interactions of random noise and signal gamma ray detections, that a positron annihilation took place somewhere along the line between the detectors. The coincidences can be sorted and integrated as PET data that can be processed and/or stored via a computing system 40.

In exemplary embodiment, the scanner 10 can include a control system 50 having processing device, e.g., controller 52 for controlling an operation of the scanner. The controller 52 of the control system 50 can be programmed to control an operation of the MRI components 16, PET components 18, and/or bed 20. While the control system 50 is depicted as being included in the scanner 10, those skilled in the art will recognize that the control system, or portions thereof, can be implemented separately and apart from the scanner 10 and can be communicatively coupled to the scanner 10. The control system 50 can be in communication with a computing device 40 such that the scanner 10 can be controlled, via a computing system 40 communicatively coupled to the control system 50 to transmit data and/or commands to the control system to control an operation of the scanner 10. In some embodiments, the computing device 40 can be in communication with the control system 50 via a communications network 54.

In exemplary embodiments, the computing system 40 can configure and/or program the control system 50 to control the MRI components 16, PET components 18, and/or the bed 20 to perform a scan sequence in response to instructions, commands, and/or requests transmitted to the control system 50 by the computing device 40. For example, RF pulses of a scan sequence for acquisition of MR images can have a timing, strength, and shape corresponding to a timing and length of a data acquisition window over which the MR data is to be acquired. Gradient pulses can be produced during the MR data acquisition by controlling one or more physical gradient coils in a gradient coil assembly 24 to produce magnetic field gradients to spatially encode acquired MR data output from the scanner 10 in one or more lines of k-space. MR signals resulting from the excitation pulses, emitted by excited nuclei in a subject, can be sensed by the coil assembly 28, and can be provided to the computing system for processing. MR data can be collected and output as one or more sets of raw k-space data. The raw k-space data can be utilized in reconstruction (e.g., via Fourier transform) of MR image data by the computing device 40 and/or another device.

A field of view (FOV) of the MR data acquisition can be controlled by the control system 50 (e.g., via the computing device 40). In exemplary embodiments, when a single MR FOV is acquired over different bed positions, the MR components can be controlled by the control system 50 in response to a change in the bed position to shift the FOV based on a distance that the bed moved. The FOV can be coextensive with the MRI spatial coverage region or can be specified to be smaller than the MRI spatial coverage region. The FOV defines the imaging area of the MRI scanner such that portions of the subject that are within the FOV are imaged by the MRI scanner. A location of the FOV can be controlled by, for example, controlling a frequency of the MR receiver and/or a phase of the MR MR receiver (e.g., via the computing device 40 and/or control system 50).

In exemplary embodiments, the control system 50 can be programmed to acquire a sequence of PET images and to acquire a portion of MR k-space concurrently (e.g., simultaneously, interleaved, etc.) with each PET image acquisition. The acquisition of each portion of k-space can be performed concurrently with an acquisition of a PET image such that multiple PET images can be acquired for a single MR image stack. For example, a subject (e.g., a patient) can rest upon the bed 20 and the bed can be moved along the longitudinal axis L into the scanner 10 at the proximate end 12 to position the subject at a first location with respect to the spatial coverage regions of the MRI components 16 and the PET components 18. A PET image can be acquired over the PET spatial coverage region to image a first portion of the subject and a portion of the MR data (k-space) corresponding to the MRI spatial coverage region can be acquired. Subsequently, the bed 20 can be moved along the longitudinal axis L further into the scanner 10 to position the subject at a second location with respect to the spatial coverage regions of the MRI components 16 and the PET components 18. A second PET image can be acquired over the PET spatial coverage region with the subject at the location to image a second portion of the subject and a portion of the MR data corresponding to the MRI spatial coverage region can be acquired. The portions of MR data can be combined to fill k-space in order to reconstruct an MR image. By segmenting the acquisition of k-space over multiple PET data acquisitions, the combined PET-MRI scanner 10 can be efficiently utilized since an acquisition of a complete k-space data set can take a longer time than the acquisition of a PET image.

Figure 2:
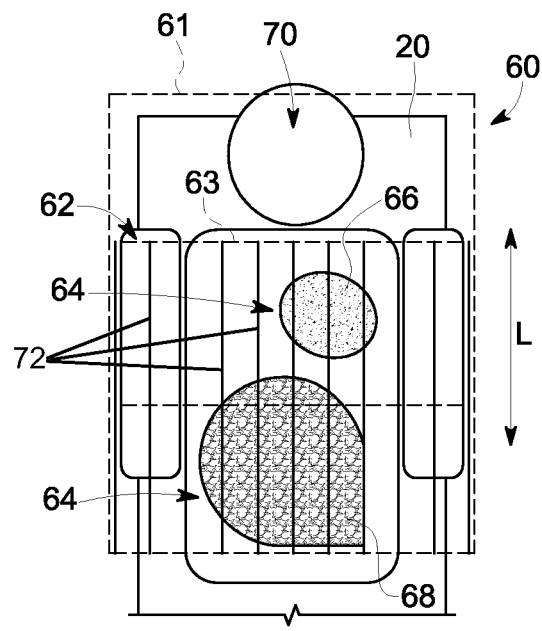
FIG. 2 illustrates a bed of an embodiment of the scanner of FIG. 1 at a first position with respect to a spatial coverage of PET imaging components and a spatial coverage associated with the MRI components.
Figure 3:
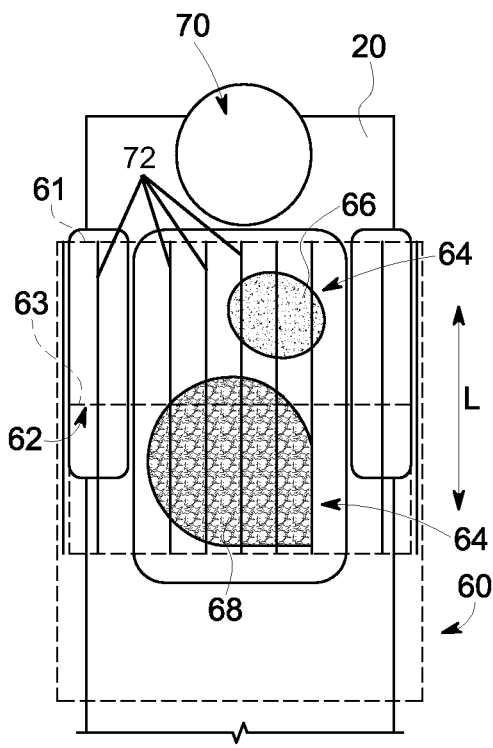
FIG. 3 illustrates a bed of an embodiment of the scanner of FIG. 1 at a second position with respect to a spatial coverage of PET imaging components and a spatial coverage associated with MRI components.

FIGS. 2 and 3 illustrate exemplary positions of the bed 20 of the scanner 10 with respect to an exemplary MRI spatial coverage region 60 associated with the MRI components 16 (FIG. 1) and a PET spatial coverage region 62 associated with the PET imaging components 18 (FIG. 1). Referring to FIGS. 2 and 3, a dashed rectangle 61 is illustrative of a perimeter of the MRI spatial coverage region 60 and a dashed rectangle 63 is illustrative of a perimeter of the PET spatial coverage region 62. As shown in FIGS. 2 and 3, the MRI spatial coverage region 60 can be larger than the PET spatial coverage region 62 and the MRI spatial coverage region 60 and PET spatial coverage region 62 can overlap and/or the MRI spatial coverage region 60 can encompass the PET spatial coverage region 62. Since the MRI spatial coverage region 60 is larger than the PET spatial coverage region 62 in the present embodiment, the MRI components 16 can acquire a larger imaging area than the PET components 18. While the MRI spatial coverage region 60 and the PET spatial coverage region 62 overlap in the present embodiment, those skilled in the art will recognize that embodiments of the scanner 10 can be implemented such that the spatial coverage regions 60, 62 are spaced away from each. Furthermore, those skilled in the art will recognize that the size of the spatial coverage regions 60, 62 can be different for different embodiments of the scanner 10.

In exemplary embodiments, when areas 64 (e.g., the heart 66 and liver 68) of a human body 70 to be scanned by the PET scanner components 18 exceed the PET spatial coverage region 62, the bed 20 of the scanner 10 can be sequentially positioned (via the control system 50) to move the human body 70 with respect to the PET spatial coverage area 62. For example, the bed 20 can be positioned at a first location along the longitudinal axis L to acquire PET data corresponding to a first portion of the human body 70 within the PET spatial coverage region 62 (FIG. 2) and can be positioned at a second location along the longitudinal axis to acquire PET data corresponding a second adjacent portion of the human body 70 within the PET spatial coverage region 62 (FIG. 3) such that the bed 20 can be sequentially positioned to align and acquire PET images for different areas of the human body 70. For example, FIG. 2 illustrates the bed 20 of the scanner 10 (and the human body 70) at the first position with respect to the PET spatial coverage region 62 to acquire a PET image of the heart 66 and FIG. 3 illustrates the bed 20 (and the human body 70) at the second position with respect to the PET spatial coverage region 62 to acquire a PET image of the liver 68. The first and second positions of the bed 20 can be specified such that adjacent areas of the body 70 are scanned. In some embodiments, an overlap can exist between the first and second positions of the bed 20 such that PET data for a portion of the body 70 that is within the PET spatial coverage region in both the first and second positions of the bed 20 is acquired twice. In some embodiments, there is no overlap between the first and second positions of the bed 20.

In the present embodiment, the heart 66 and the liver 68 can be encompassed within the MRI spatial coverage region 60 such that MR data can be acquired to generate MR images for the heart 66 and liver 68 without repositioning the bed 20. A time period over which MR data is acquired for a FOV in the MRI spatial coverage region 60 (e.g., a time required to acquire a complete k-space data set corresponding to a FOV within the MRI spatial coverage region) can be greater than a time period over which PET data is acquired for the PET spatial coverage region 62 such that a duration of a concurrent acquisition of MR data and PET data over their respective spatial coverage regions 60, 62 can be dependent on the time period over which the MR data is acquired for the MRI spatial coverage region. For example, with reference to FIG. 2, the bed 20 of the scanner 10 (and the human body 70) at the first position with respect to the MRI spatial coverage region to acquire an MR image of the FOV including the heart 66 and liver 68 and with respect to the PET spatial coverage region 62 to concurrently acquire a PET image of the heart 66. Subsequently, with reference to FIG. 3, the bed 20 (and the human body 70) can be moved to the second position to align the liver with the PET spatial coverage 62 and a PET image of the liver 68 can be acquired. The above approach can result in an inefficient and time consuming image acquisition process; particularly, when PET images are to be acquired for different areas of the body 70 (e.g., the heart 66 and the liver 68).

In exemplary embodiments of the present disclosure, with reference to FIGS. 2 and 3, the scanner 10 can be programmed (e.g., by the computing device 40) to partition the acquisition of the MR data for a specified FOV into a sequence of temporally separate acquisitions such that a portion of the MR data for the specified FOV is acquired during a first time period and one or more other portions of the MR data for the specified FOV are acquired during one or more subsequent time periods and/or when a position of the bed has changed. PET data can be acquired corresponding to the PET spatial coverage region 62 during one or more of the time periods. For example, an acquisition of each portion of the MR data can be performed concurrently with an acquisition of PET data such that multiple sets of PET data can be acquired for MR data acquisition of single FOV. For example, with reference to FIG. 2, the bed 20 of the scanner 10 (and the human body 70) can be moved to the first position with respect to the MRI spatial coverage region 60 and PET spatial coverage region 62 to acquire a first portion of the k-space corresponding to a FOV including the heart 66 and liver 68 and to concurrently acquire PET data of the heart 66 and surrounding areas within the PET spatial coverage region 60. Subsequently, with reference to FIG. 3, the bed 20 (and the human body 70) can be moved to the second position with respect to the MRI spatial coverage region 60 and PET spatial coverage region 62 to acquire second portion of the k-space corresponding the FOV including the heart 66 and liver 68 and to concurrently acquire PET data of the liver 68 and surrounding areas within the PET spatial coverage region 62.

Lines 72 in FIGS. 2 and 3 are illustrative of an exemplary MRI field of view (FOV) over which the first and second portions of k-space can be acquired during each acquisition time period and according to one embodiment of the present disclosure. The location of the MRI FOV can be determined by controlling a frequency and/or a phase of the MR receiver (e.g., via the computing device 40 and/or control system 50). The first and second portions of k-space corresponding to the FOV can be combined and can be used to reconstruct a stack of MR images of heart 66 and liver 68. To maintain a substantially identical FOV location for different bed positions, the FOV can be shifted within the MRI spatial coverage region 60 so that a specified area of the body 70 can be imaged at the different bed positions using the MRI components 16. If MR data is to be acquired for the heart 66 and the liver 68, the FOV when the bed 20 is in the first and second positions can be specified using the gradient coils to acquire MR data of the area of the body 70 corresponding to the heart 66 and liver 68. For example, the FOV can be shifted away from the magnet isocenter in one direction along the longitudinal axis while the bed 20 is in the first position, and the FOV can be shifted in the opposite direction when the bed 20 is moved to the second position so that the FOV covers a substantially identical area of the body 70 in both bed positions. If the gradient readout direction for the MRI pulse sequence is in the head-foot direction (e.g., along the longitudinal axis), the FOV shift can be accomplished by changing the MR receiver frequency during readout. If the gradient readout direction is orthogonal to the head-foot direction (e.g., transverse to the longitudinal axis), the shift in the FOV can be accomplished by changing a phase of MR signal reception.

Figures 4A, 4B, 4C:
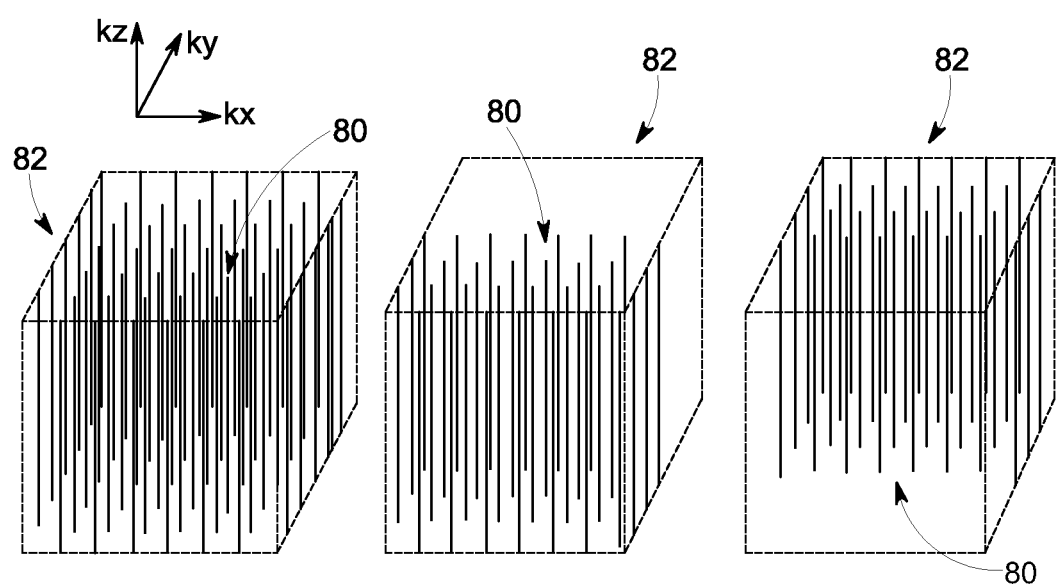
FIG. 4A illustrates exemplary lines of k-space data corresponding to a readout of a magnetic resonance image capture.
FIG. 4B illustrates exemplary lines of half of the k-space data corresponding to a readout of a magnetic resonance image capture at a specified bed position.
FIG. 4C illustrates exemplary lines of a complementary half of the k-space data to FIG. 4B corresponding to a readout of a magnetic resonance image capture at another specified bed position.

FIGS. 4A-C are illustrative of MR data acquisition in lines 80 of a 3D k-space 82. FIG. 4A illustrates a full MR data acquisition in 3D k-space (e.g., all of the lines of k-space are acquired). FIG. 4B illustrates a half MR data acquisition in 3D k-space for the specified FOV (e.g., a first half of the lines of k-space are acquired) while bed 20 is in the first position shown in FIG. 2. FIG. 4C illustrates a complementary MR data acquisition in 3D k-space for the specified FOV compared to FIG. 4B (e.g., a second half of lines of k-space for the specified FOV are acquired) while bed is in the second position shown in FIG. 3. In some embodiments, a quantity of lines of k-space acquired at each bed position can vary. As one example, two thirds of the lines of k-space can be acquired in the first position of the bed 20 and the remaining one third of the lines of k-space can be acquired in the second position of the bed 20 or vice versa.

In exemplary embodiments, a 3D fast gradient echo sequence can be run with gradient readout oriented in the head-foot direction (e.g., along the longitudinal axis), with raw-data or k space filled as shown in FIGS. 4B-C. The receiver frequency can be offset to shift the FOV in one direction for those lines 80 of k-space 82 acquired while the bed is in the first position, and the frequency is offset by the substantially identical amount in the opposite direction to shift the FOV in the opposite direction for the lines 80 of k-space 82 acquired while the bed is in the second position. If the gradients are linear, the MR data sets can be combined and reconstructed to form a stack of images.

If the gradients of the MR acquisitions are not linear, the lines of k-space acquired while the bed 20 is in the different positions can be at least partially incompatible with each other. When k-space sampling is partitioned between different bed positions, the lines from each bed position can be Fourier transformed to yield under-sampled complex images (which typically show aliasing artifacts), and each stack of aliased complex images can be unwarped. When the two under-sampled complex images from each slice position are added or combined, the aliasing artifacts can cancel, and a stack of fully sampled images result, with improved signal-to-noise ratio (SNR) relative to the individual stacks.

Alternatively, for the sampling scheme shown in FIG. 4B-C, the k-space lines acquired in the first bed position (FIG. 4B) can be reconstructed into a stack of MR images using a half-Fourier method such as homodyne reconstruction, and a gradient unwarping algorithm applied to straighten the MR images. The second set of k-space lines (FIG. 4C) can similarly be reconstructed into a stack of MR images and unwarped to straighten the MR images. The MR images from each bed position can be added to provide the final stack of images. While FIG. 4A-C are illustrative of a Cartesian k-space trajectory, those skilled in the art will recognize that non-Cartesian trajectories can be implemented. For example, in exemplary embodiments, a spiral trajectory, cone trajectory, radial trajectory, and/or other suitable non-Cartesian k-space trajectories can be implemented. Portions of the non-Cartesian trajectories can be acquired and can be used to generate one or more stacks of MR images. For example, half of non-Cartesian k-space can be acquired when the bed is in the first position and a second half of non-Cartesian k-space can be acquired when the bed is in the second position.

Figure 5:
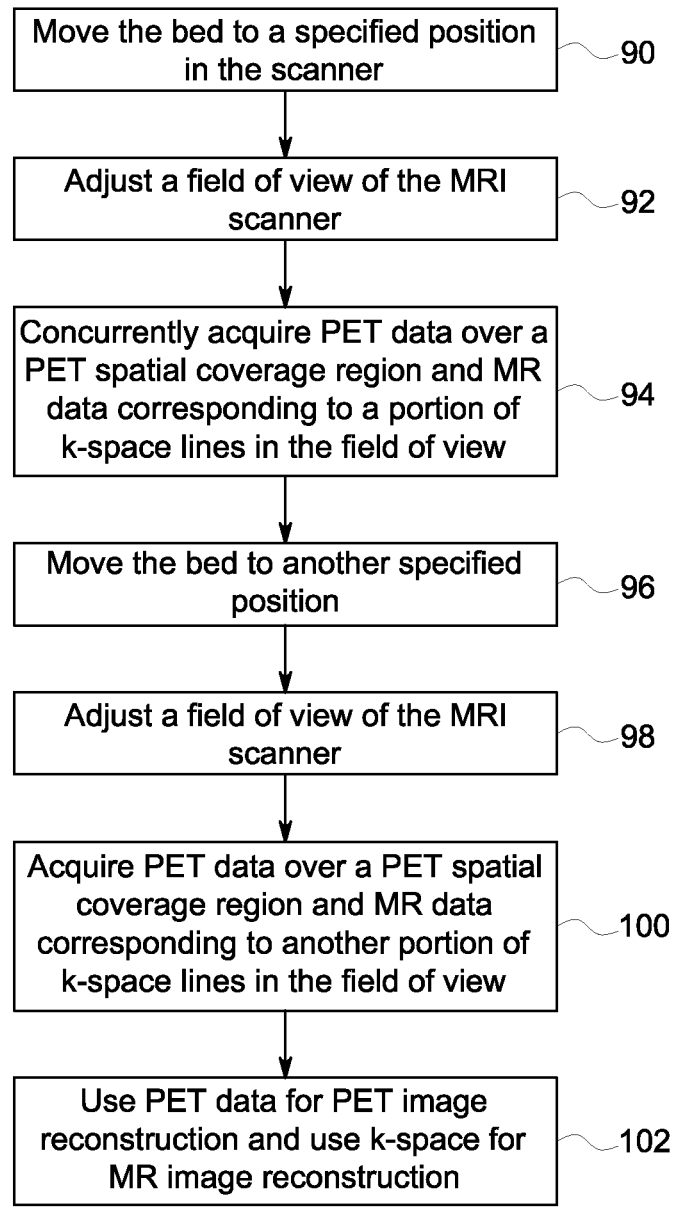
FIG. 5 is a flowchart of an exemplary image capturing process in accordance with exemplary embodiments of the present disclosure.

FIG. 5 is a flowchart of an exemplary acquisition process for concurrent acquisition of PET and MR data. A PET agent can be administered to the imaging subject (e.g., a human patient) and the subject can be positioned on the bed of the scanner. The bed can be advanced into the PET-MR scanner along the longitudinal through the proximal end of the scanner to position the bed and the subject at a first location along the longitudinal axis to align a first area of the subject (e.g., the heart) with the PET and MRI spatial coverage regions (step 90). A field of view (FOV) position can be specified and the FOV position of the MRI scanner can be adjusted (e.g., shifted) to correspond to a specified area of the subject for which MR images are to be acquired (step 92). PET data and MR data can be acquired concurrently when the bed is at the first location (step 94). For example, PET data can be acquired over the PET spatial coverage region and MR data corresponding to a portion of k-space from the FOV can be acquired.

After the PET data and MR data have been acquired from the first bed position, the bed can be advanced further into the scanner along the longitudinal axis and towards the distal end of the scanner to position the bed at a second location (step 96). At the second location, a second area of the subject can be aligned with the PET spatial coverage region. In exemplary embodiments, the second area of the subject can be adjacent to the first area of the subject or can be spaced away from the first area of the subject. The FOV position can be adjusted (e.g., shifted) to position the FOV with respect to the specified area of the subject for which MR images are to be acquired (e.g., an identical or substantially identical area as that of the first bed position) (step 98). PET data and MR data can be acquired concurrently when the bed is at the second location (step 100). For example, PET data can be acquired over the PET spatial coverage region and MR data corresponding to a portion of k-space from the FOV can be acquired. The PET data acquired for the first and second areas of the body can be used to generate PET images of the first and second areas and MRI images can be generated using the portions of k-space acquired for the first and second bed positions as described herein such that multiple sets of PET data can be acquired for different areas of the subject for an MRI acquisition of a single FOV (step 102).

While exemplary embodiments include partitioning MRI acquisition of a FOV over two bed locations, those skilled in the art will recognize that other combinations of fields of view can be implemented. For example, in exemplary embodiments, PET data can be acquired for three bed positions concurrently with MRI acquisitions of two MR fields of view from different locations, where the total coverage in the foot-head direction is the same for PET and MR. Furthermore, exemplary embodiments can be implemented using continuously-moving-bed imaging, where both the PET and MR data are acquired continuously as the bed moves.

Figure 6:
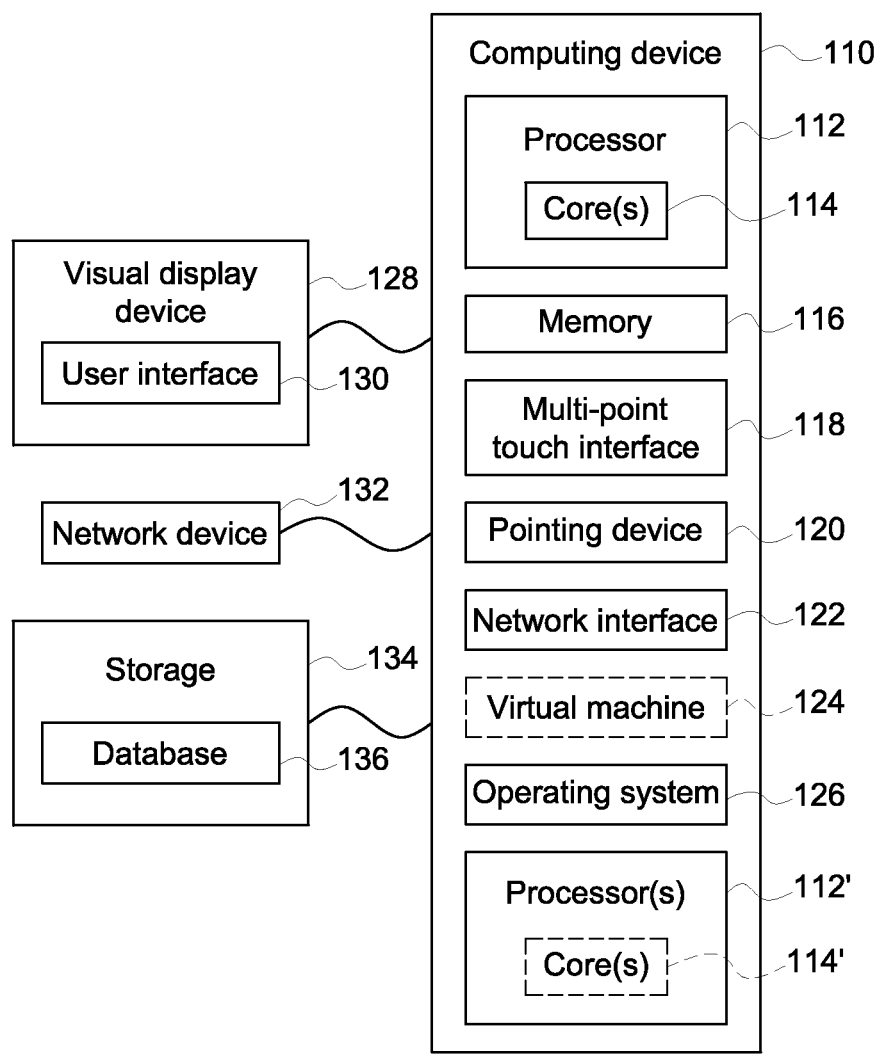
FIG. 6 is an exemplary computing system for implementing exemplary embodiments of the present disclosure.

FIG. 6 is a block diagram of an exemplary computing device 110 that may be used to implement exemplary embodiments of the present disclosure. The computing device 110 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 116 included in the computing device 110 may store computer-readable and computer-executable instructions or software for interface with and/or controlling an operation of the scanner 10. The computing device 110 also includes configurable and/or programmable processor 112 and associated core 114, and optionally, one or more additional configurable and/or programmable processing devices, e.g., processor(s) 112' and associated core(s) 114' (for example, in the case of computer systems having multiple processors/cores), for executing computer-readable and computer-executable instructions or software stored in the memory 116 and other programs for controlling system hardware. Processor 112 and processor(s) 112' may each be a single core processor or multiple core (114 and 114') processor.

Virtualization may be employed in the computing device 110 so that infrastructure and resources in the computing device may be shared dynamically. A virtual machine 124 may be provided to handle a process running on multiple processors so that the process appears to be using only one computing resource rather than multiple computing resources. Multiple virtual machines may also be used with one processor.

Memory 116 may include a computer system memory or random access memory, such as DRAM, SRAM, EDO RAM, and the like. Memory 116 may include other types of memory as well, or combinations thereof.

A user may interact with the computing device 110 through a visual display device 128, such as a computer monitor, which may display one or more user interfaces 130 that may be provided in accordance with exemplary embodiments. The computing device 110 may include other I/O devices for receiving input from a user, for example, a keyboard or any suitable multi-point touch interface 118, a pointing device 120 (e.g., a mouse). The keyboard 118 and the pointing device 120 may be coupled to the visual display device 128. The computing device 110 may include other suitable conventional I/O peripherals.

The computing device 110 may also include one or more storage devices 134, such as a hard-drive, CD-ROM, or other computer readable media, for storing data and computer-readable instructions and/or software that interface with and/or control an operation of the scanner 10 described herein. Exemplary storage device 134 may also store one or more databases for storing any suitable information required to implement exemplary embodiments. For example, exemplary storage device 134 can store one or more databases 136 for storing information, such as scan sequences, MR data, PET data, MR images, PET images, and/or any other information that can be used to implement exemplary embodiments of the present disclosure. The databases may be updated by manually or automatically at any suitable time to add, delete, and/or update one or more items in the databases.

The computing device 110 can include a network interface 122 configured to interface via one or more network devices 132 with one or more networks, for example, Local Area Network (LAN), Wide Area Network (WAN) or the Internet through a variety of connections including, but not limited to, standard telephone lines, LAN or WAN links (for example, 802.11, T1, T3, 56kb, X.25), broadband connections (for example, ISDN, Frame Relay, ATM), wireless connections, controller area network (CAN), or some combination of any or all of the above. The network interface 122 may include a built-in network adapter, network interface card, PCMCIA network card, card bus network adapter, wireless network adapter, USB network adapter, modem or any other device suitable for interfacing the computing device 110 to any type of network capable of communication and performing the operations described herein. Moreover, the computing device 110 may be any computer system, such as a workstation, desktop computer, server, laptop, handheld computer, tablet computer, or other form of computing or telecommunications device that is capable of communication and that has sufficient processor power and memory capacity to perform the operations described herein.

The computing device 110 may run any operating system 126, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 126 may be run in native mode or emulated mode. In an exemplary embodiment, the operating system 126 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A combined positron emission tomography (PET) and magnetic resonance imaging (MRI) system comprising:
    PET imaging components forming a PET scanner portion of the combined PET-MRI scanner;
    MRI components forming an MRI scanner portion of the combined PET-MRI scanner;
    a support structure disposed and moveable with respect to a PET spatial coverage region associated with the PET scanner portion and a MRI spatial coverage region associated with the MRI scanner portion;
    a controller in communication with the PET imaging components and the MRI components to control the MRI scanner portion to partition an acquisition of MR data for a MRI field of view (FOV) within the MRI spatial coverage region over a sequence of PET data acquisitions from smaller PET fields of view and to acquire the MR data for the MRI field of view concurrently with an acquisition of different sets of the PET data; and
    the controller being configured to control acquisition of PET data and MR data based on a position of the support structure including wherein both the PET data and MR data are acquired continuously as the support structure moves, wherein a single MR image stack is acquired concurrently with the different sets of the PET data, the single MR image stack corresponding to the MRI FOV, the PET spatial coverage region corresponding to the different sets of the PET data, the MRI spatial coverage region larger than the PET spatial coverage region, wherein the different sets of PET data include a first set acquired at a first position of the support structure and a second set acquired at a second position of the support structure, the first and second sets of PET data corresponding to different portions of a patient body, wherein the first position and the second position differ with respect to the PET imaging components and the MRI imaging components, wherein the first position and second position differ with respect to the MRI spatial coverage region, wherein the controller is configured to shift a focus of the MRI FOV with respect to the MRI spatial coverage region to acquire the MR data for the MRI FOV for a same area of the patient body at both the first position and the second position.

2. The system of claim 1, wherein an acquisition of the MR data for the field of view is apportioned over the first and second positions, wherein the controller is configured to shift the MRI FOV from a magnet isocenter in one direction for the first position and to shift the MRI FOV away from the magnet isocenter in an opposite direction for the second position.

3. The system of claim 1, wherein the MR data acquired with respect to the first position represents a first portion of k-space for the area of the patient body and the MR data acquired with respect to the second position represents a second portion of k-space for the area of the patient body.

4. The system of claim 3, wherein the controller is programmed to control the MRI scanner to acquire the first portion of k-space concurrently with the first PET data acquisition and to acquire the second portion of k-space concurrently with the second PET data acquisition.

5. The system of claim 4, wherein the first portion of k-space corresponds to half of k-space and the second portion of k-space corresponds to a remaining half of k-space.

6. The system of claim 1, wherein the MRI scanner comprises gradient coils and the controller is programmed to control the gradient coils to acquire k-space data for the MRI field of view.

7. The system of claim 1, wherein the MR data are acquired on a Cartesian trajectory through k-space.

8. The system of claim 1, wherein the MR data are acquired on a non-Cartesian trajectory through k-space.

9. A method of capturing positron emission tomography (PET) images and magnetic resonance (MR) images with a combined PET-MRI scanner comprising:
acquiring a first portion of MR data from a MR field of view concurrently with a first acquisition of PET data, the first acquisition of PET data acquired at a first position of a support structure;
adjusting a position the MR field of view in response to a change in a location of the support structure of the combined PET-MRI scanner; and
acquiring a second portion of MR data from the MR field of view concurrently with a second acquisition of PET data, the second acquisition of PET data acquired at a second position of the support structure, the first and second acquisitions of PET data corresponding to different portions of a patient body, wherein the first position and the second position differ with respect to PET imaging components and MRI imaging components, wherein the first position and second position differ with respect to the MRI spatial coverage region, wherein the second acquisition of PET data and the second portion of MR data are acquired continuously as the support structure moves, wherein a single MR image stack is acquired concurrently with the first acquisition of PET data and the second acquisition of PET data, the single MR image stack corresponding to an MRI spatial coverage region associated with an MRI scanner portion of the combined PET-MRI scanner, the first and second acquisitions of PET data corresponding to a PET spatial coverage region associated with a PET scanner portion of the combined PET-MRI scanner, the MRI spatial coverage region larger than the PET spatial coverage region, and wherein a focus of the MR field of view with respect to the MRI spatial coverage region is shifted to acquire the MR data for the MR field of view for a same area of the patient body at both the first position and the second position.

10. The method of claim 9, wherein the first portion of MR data acquired from the field of view represents a first portion of k-space and the second portion of MR data acquired from the field of view represents a second portion of k-space.

11. The method of claim 10, wherein the first portion of k-space corresponds to half of k-space and the second portion of k-space corresponds to a remaining half of k-space.

12. The method of claim 9, further comprising:
reconstructing the first portion of MR data acquired from the field of view to generate a first stack of MR images;
reconstructing the second portion of MR data acquired from the field of view to generate a second stack of MR images; and
combining the first and second stacks to form the single MR image stack having reduced aliasing in comparison to the first and second stacks.

13. The method of claim 12, further comprising unwarping the MR images of the first and second stacks prior to combining the first and second stacks.

14. The method of claim 9, further comprising:
combining the MR data for the first and second portions of the field of view; and reconstructing the MR data acquired for the first and second portions of the field of view to generate the single MR image stack.

15. The method of claim 9, wherein adjusting a position of the MR field of view comprises shifting the field of view to align with an area of a subject for which the MR data for the field of view is acquired.

16. The method of claim 15, wherein shifting the field of view comprises at least one of adjusting an MR receiver frequency or phase of the combined PET-MRI scanner during MR signal reception.

17. The method of claim 9, further comprising:
adjusting a position the MR field of view in response to another change in the location of the bed of the combined PET-MRI scanner; and
acquiring a third portion of MR data from the MR field of view concurrently with a third acquisition of PET data.

18. The method of claim 9, wherein the MR data are acquired on at least one of a Cartesian or a non-Cartesian trajectory through k-space.

* * * * *